United States Patent
Osawa et al.

(10) Patent No.: US 8,415,639 B2
(45) Date of Patent: Apr. 9, 2013

(54) QUANTUM EFFICIENCY MEASUREMENT METHOD, QUANTUM EFFICIENCY MEASUREMENT APPARATUS, AND INTEGRATOR

(75) Inventors: Yoshihiro Osawa, Moriyama (JP); Kazuaki Ohkubo, Kusatsu (JP)

(73) Assignee: Otsuka Electronics Co., Ltd., Hirakata-shi (JP)

( * ) Notice: Subject to any disclaimer, the term of this patent is extended or adjusted under 35 U.S.C. 154(b) by 269 days.

(21) Appl. No.: 13/033,612

(22) Filed: Feb. 24, 2011

(65) Prior Publication Data

US 2011/0226961 A1   Sep. 22, 2011

(30) Foreign Application Priority Data

Mar. 18, 2010   (JP) .................................. 2010-061804

(51) Int. Cl.
*G01J 1/58*   (2006.01)
(52) U.S. Cl.
USPC .................... 250/458.1; 250/459.1; 250/336.1
(58) Field of Classification Search ................ 250/458.1, 250/459.1, 336.1
See application file for complete search history.

(56) References Cited

U.S. PATENT DOCUMENTS

2007/0242264 A1*   10/2007   Ohkubo ........................ 356/213

FOREIGN PATENT DOCUMENTS

| JP | 9-292281 | | 11/1997 |
| JP | 09292281 A | * | 11/1997 |
| JP | 10-142152 | | 5/1998 |
| JP | 10-293063 | | 11/1998 |

OTHER PUBLICATIONS

Kazuaki Ohkubo and Teruaki Shigeta, "Absolute Flurorescent Quantum Efficiency of NBS Phospor Standard Samples", Journal of Illuminating Engineering Institute of Japan, The Illuminating Engineering Institute of Japan, Feb. 1999, vol. 83, No. 2, pp. 87-93 (English abstract included).

* cited by examiner

*Primary Examiner* — David Porta
*Assistant Examiner* — Gisselle Gutierrez
(74) *Attorney, Agent, or Firm* — Ditthavong Mori & Steiner, P.C.

(57) ABSTRACT

A quantum efficiency measurement method includes the steps of: disposing a sample at a predetermined position in an integrator having an integrating space; applying excitation light to the sample and measuring a spectrum in the integrating space as a first spectrum through a second window; configuring an excitation light incident portion so that excitation light after having passed through the sample is not reflected in the integrating space; applying the excitation light to the sample and measuring a spectrum in the integrating space as a second spectrum through the second window; and calculating a quantum efficiency of the sample based on a component constituting a part of the first spectrum and corresponding to a wavelength range of the excitation light, and a component constituting a part of the second spectrum and corresponding to a wavelength range of light generated by the sample from the received excitation light.

9 Claims, 12 Drawing Sheets

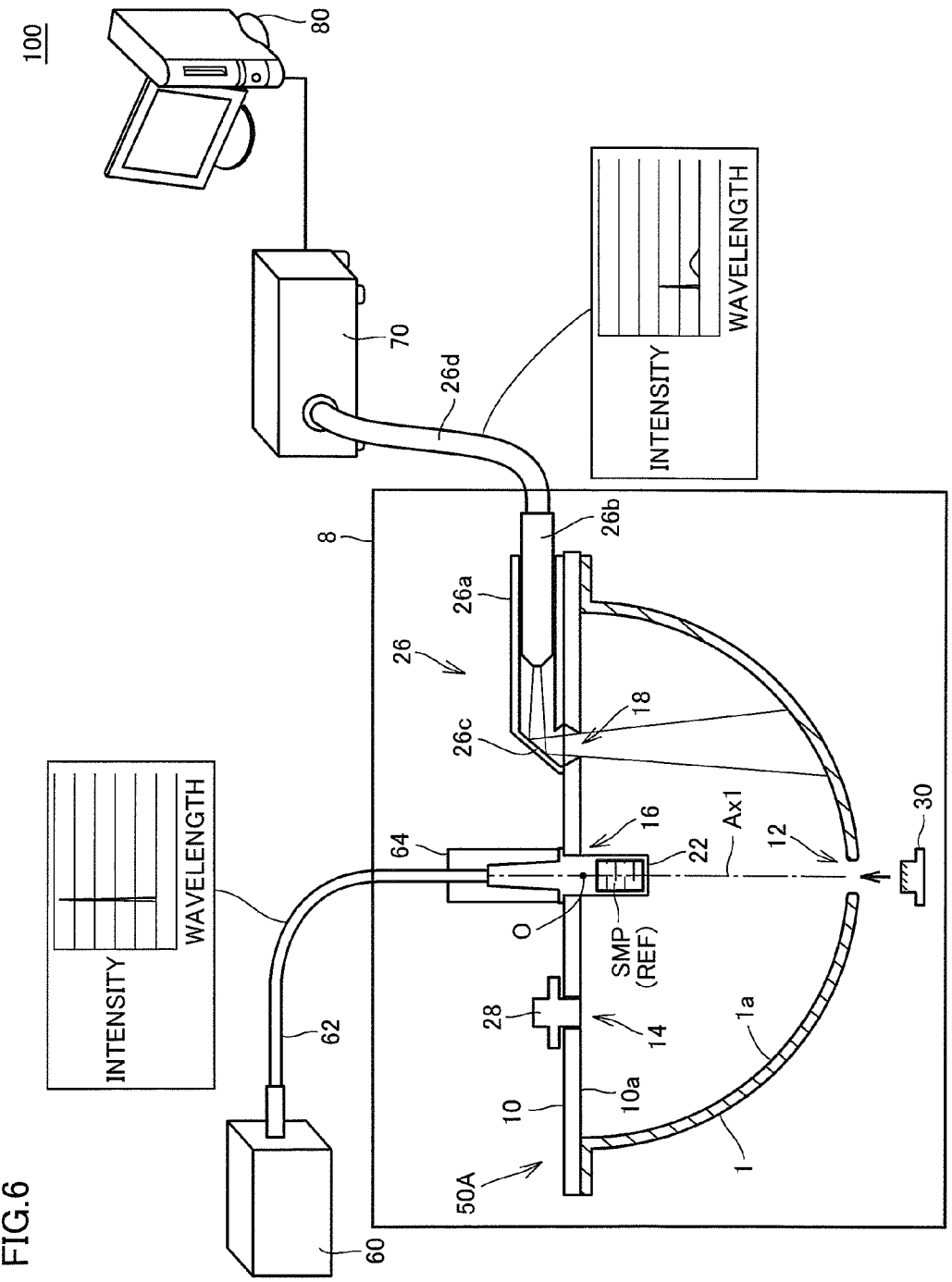

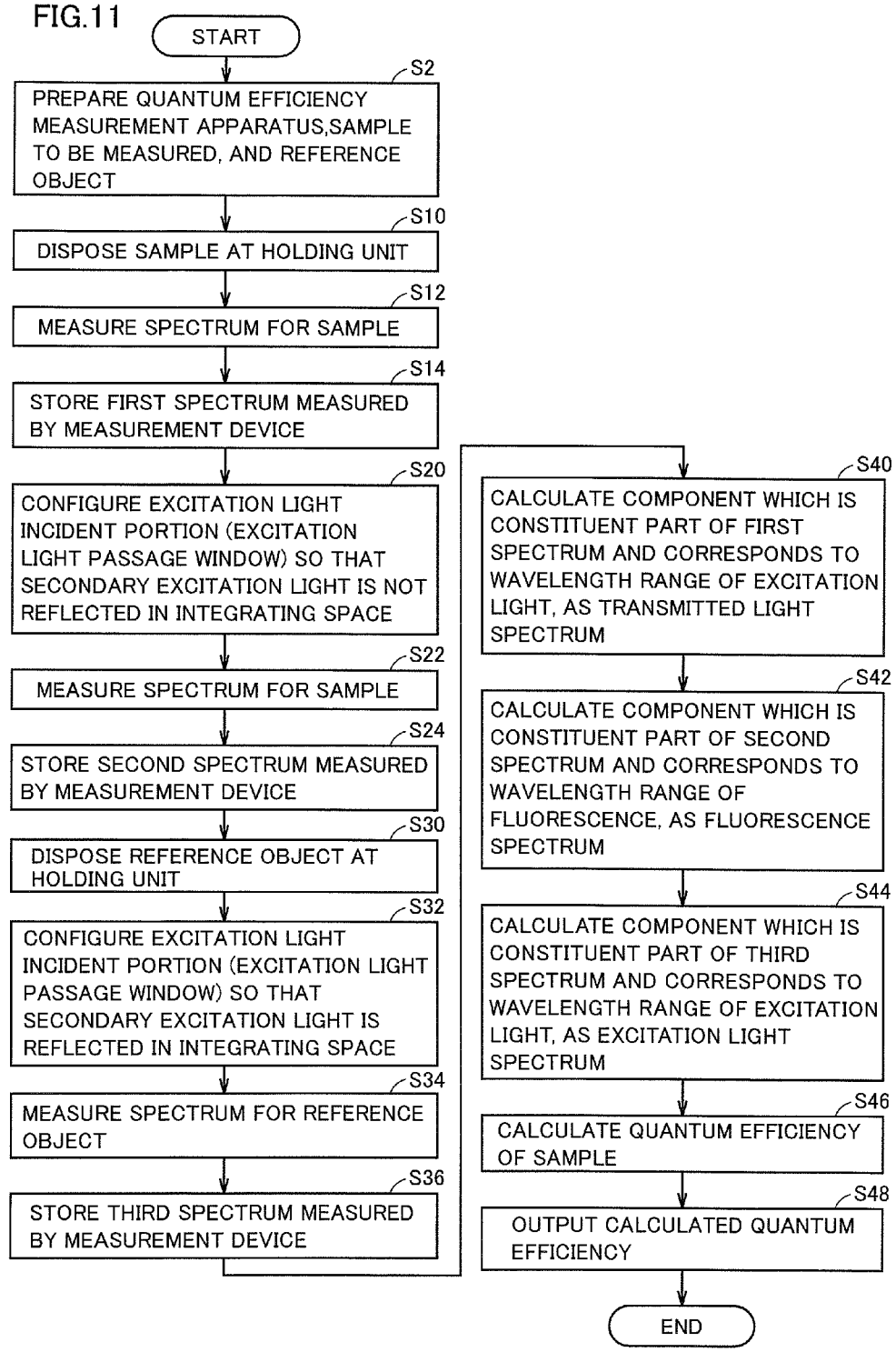

QUANTUM EFFICIENCY MEASUREMENT METHOD, QUANTUM EFFICIENCY MEASUREMENT APPARATUS, AND INTEGRATOR

BACKGROUND OF THE INVENTION

1. Field of the Invention

The present invention relates to a method and an apparatus for measuring the quantum efficiency, and an integrator directed thereto.

2. Description of the Background Art

In recent years, development of fluorescent lamp and display has been advancing rapidly. With such development, the quantum efficiency has become of interest as an indicator for more accurately evaluating the performance of a phosphor used for the lamp and display. In general, the quantum efficiency refers to the ratio of the number of photons generated from a sample (typically phosphor) to the number of photons absorbed by the sample.

For example, Ohkubo and Shigeta, "Absolute Fluorescent Quantum Efficiency of NBS Phosphor Standard Samples," Journal of the Illuminating Engineering Institute of Japan, The Illuminating Engineering Institute of Japan, 1999, Vol. 83, No. 2, pp. 87-93, discloses a typical configuration for measuring the quantum efficiency. Instead of such a typical configuration, Japanese Patent Laying-Open Nos. 09-292281, 10-142152, and 10-293063 for example each disclose an alternative configuration for measuring the quantum efficiency.

The configuration for measuring the quantum efficiency as described above is adapted chiefly to measurement of the quantum efficiency of a solid sample, or a sample molded in the form of a solid. Specifically, the quantum efficiency of the sample is measured by applying excitation light to the sample and acquiring fluorescence emitted from the sample.

For example, phosphors used for EL (Electro Luminescent) emission are powder phosphors in many cases. In such cases, a powder sample is dissolved in a solvent and the quantum efficiency of the sample in the form of the solution is measured. For measurement of the quantum efficiency of such a solution, the solution sample is enclosed in a translucent container, and then excitation light is applied to the solution sample in the container to cause fluorescence to be generated.

Such a measurement system, however, may involve a problem of measurement errors due to re-excitation (secondary excitation). Specifically, a phenomenon may occur in which the excitation light after having passed through the solution sample is reflected from the interior of an integrating sphere or the like and then enters again the solution sample, resulting in emission of fluorescence of an amount larger than that which should otherwise be emitted.

SUMMARY OF THE INVENTION

The present invention has been made to solve problems as described above, and an object of the invention is to provide a quantum efficiency measurement method, a quantum efficiency measurement apparatus, and an integrator directed thereto that are capable of reducing errors due to re-excitation (secondary excitation) that may occur when the quantum efficiency is measured.

A quantum efficiency measurement method according to an aspect of the present invention includes the steps of: disposing a sample at a predetermined position in an integrator having an integrating space; applying excitation light to the sample disposed at the predetermined position, through a first window provided at the integrator, and measuring a spectrum in the integrating space as a first spectrum, through a second window provided at a position of the integrator, the position of the integrator not being crossed by an optical axis of the excitation light; configuring an excitation light incident portion located opposite to the first window and crossed by the optical axis of the excitation light in the integrator, so that excitation light after having passed through the sample is not reflected in the integrating space; applying the excitation light to the sample disposed at the predetermined position through the first window and measuring a spectrum in the integrating space as a second spectrum through the second window, under a state where the excitation light is not reflected in the integrating space; and calculating a quantum efficiency of the sample based on a component constituting a part of the first spectrum and corresponding to a wavelength range of the excitation light, and a component constituting a part of the second spectrum and corresponding to a wavelength range of light generated by the sample from the excitation light received by the sample.

Preferably, the excitation light incident portion of the integrator has a third window formed to pass the excitation light, and the step of configuring includes the step of removing a plug member having closed the third window, the plug member having a reflection characteristic substantially identical to that of an inner surface of the integrator.

Preferably, the method further includes the steps of disposing a reference object at the predetermined position; and applying the excitation light to the reference object disposed at the predetermined position through the first window, and measuring a spectrum in the integrating space as a third spectrum through the second window. The step of calculating a quantum efficiency of the sample includes the step of calculating, as an optical component absorbed by the sample, a difference between a component constituting a part of the first spectrum and corresponding to the wavelength range of the excitation light, and a component constituting a part of the third spectrum and corresponding to the wavelength range of the excitation light.

A quantum efficiency measurement apparatus according to another aspect of the present invention includes: an integrator having an integrating space in the integrator; a light source for applying excitation light into the integrating space through a first window provided at the integrator; a measurement device for measuring a spectrum in the integrating space through a second window provided at a position of the integrator, the position of the integrator not being crossed by an optical axis of the excitation light; a holding unit for disposing a sample or a reference object on the optical axis of the excitation light in the integrator; a switch mechanism for switching an excitation light incident portion located opposite to the first window and being crossed by the optical axis of the excitation light in the integrator, between a state of reflecting the excitation light in the integrating space and a state of non-reflecting the excitation light in the integrating space; and a processing unit for calculating a quantum efficiency of the sample, based on a first spectrum measured by the measurement device when the sample is disposed at the holding unit and the excitation light incident portion is set in the state of reflecting the excitation light, and a second spectrum measured by the measurement device when the sample is disposed at the holding unit and the excitation light incident portion is set in the state of non-reflecting the excitation light.

Preferably, the switch mechanism includes a third window provided at the excitation light incident portion of the integrator for passing the excitation light, and a plug member to be fit in the third window and having a reflection characteristic substantially identical to an inner surface of the integrator.

More preferably, the switch mechanism further includes a light absorbing portion attached from outside the integrator and in association with the third window.

Preferably, the integrator includes: a hemispherical portion having a light diffuse reflection layer on an inner surface of the hemispherical portion; and a plane mirror disposed to close an opening of the hemispherical portion. The first window is provided at one of a position involving a substantial center of curvature of the hemispherical portion and located on the plane mirror, and a position involving a vertex of the hemispherical portion.

Preferably, the integrator is a sphere having a light diffuse reflection layer on an inner surface of the sphere, and the holding unit is configured to allow the sample and the reference object to be disposed at a central portion of the sphere.

According to still another aspect of the present invention, an integrator having an integrating space in the integrator is provided. The integrator includes: a holding unit for disposing a sample or a reference object on an optical axis of excitation light applied into the integrating space through a first window; a light extraction unit for directing light through a second window provided at a position not being crossed by the optical axis of the excitation light so as to measure a spectrum in the integrating space; and a switch mechanism for switching an excitation light incident portion located opposite to the first window and being crossed by the optical axis of the excitation light in the integrator, between a state of reflecting the excitation light in the integrating space and a state of non-reflecting the excitation light in the integrating space.

In accordance with the present invention, errors due to re-excitation (secondary excitation) that may occur when the quantum efficiency is measured can be reduced.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 6 is a schematic diagram showing an entire configuration of a quantum efficiency measurement apparatus according to a first embodiment of the present invention.

FIG. 11 is a flowchart showing a procedure for measuring the quantum efficiency by means of the quantum efficiency measurement apparatus according to the first embodiment of the present invention.

DESCRIPTION OF THE PREFERRED EMBODIMENTS

Figure 1:
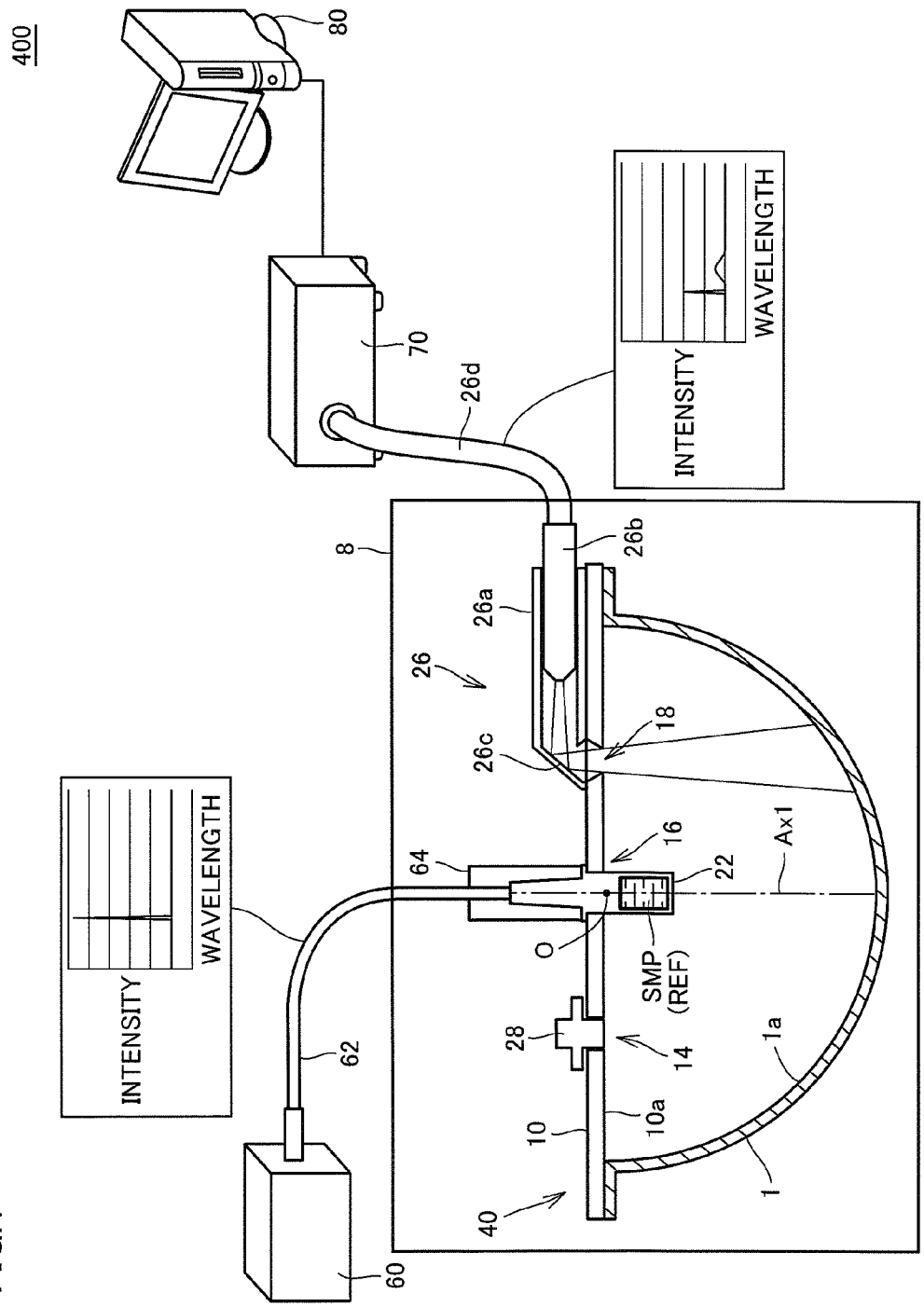
FIG. 1 is a schematic diagram showing an entire configuration of a quantum efficiency measurement apparatus relevant to the present invention.

Embodiments of the present invention will be described in detail with reference to the drawings. In the drawings, the same or corresponding components are denoted by the same reference characters, and a description thereof will not be repeated.

[A. Overview]

In a quantum efficiency measurement method according to the present embodiment, the quantum efficiency is measured by applying excitation light to a sample placed in an integrating space and measuring the resultant light (fluorescence). More specifically, under the condition where the excitation light after having passed through the sample is reflected in the integrating space, the excitation light absorbed by the sample is measured. Under the condition where the excitation light after having passed through the sample is not reflected in the integrating space, the light (fluorescence) generated from the sample is measured.

In this way, the two-stage measurement process is performed to thereby reduce measurement errors due to re-excitation (secondary excitation).

[B. Relevant Art]

Referring first to FIG. 1, a quantum efficiency measurement apparatus 400 relevant to the present invention will be described.

b1. Apparatus Configuration

FIG. 1 shows quantum efficiency measurement apparatus 400 measuring the quantum efficiency of a sample SMP by means of a hemispherical integrator 40.

Integrator 40 includes a hemispherical portion 1, and a disk-shaped plane mirror 10 disposed to involve a substantial center of curvature O of hemispherical portion 1 and close the opening of hemispherical portion 1. Integrator 40 forms an integrating space in the integrator. The center of curvature O of hemispherical portion 1 refers exemplarily to the geometric center of the inner surface side of hemispherical portion 1.

Hemispherical portion 1 has a light diffuse reflection layer 1a on its inner surface (inner wall). This diffuse reflection layer 1a is formed exemplarily by applying or spraying a light diffusing material such as barium sulfate or PTFE (polytetrafluoroethylene). On the inner surface side of hemispherical portion 1, plane mirror 10 has a reflection layer 10a that causes mirror reflection (specular reflection). As reflection layer 10a of plane mirror 10 is disposed opposite to the inner surface of hemispherical portion 1, a virtual image of hemispherical portion 1 is created. As described above, plane mirror 10 is disposed to involve the center of curvature O of hemispherical portion 1, and therefore, the virtual image created by plane mirror 10 is a hemisphere having a constant curvature. A space (real image) defined by the inner surface of hemispherical portion 1 and the virtual image created by plane mirror 10 may be combined to obtain the illuminance distribution that is substantially the same as the one which is obtained when a full-sphere type integrator is used.

In other words, in integrator 40, the space, which is a combination of the space (real image) defined by the inner surface of hemispherical portion 1 and the virtual image created by plane mirror 10, is a substantial integrating space.

Integrator 40 has a sample window 16 formed at a central portion of plane mirror 10. Quantum efficiency measurement apparatus 400 includes a light source apparatus 60 for applying excitation light into the integrating space through sample window 16 provided to integrator 40.

Light source apparatus 60 includes a light source for generating excitation light. As this light source, for example, xenon discharge lamp (Xe lamp), white LED (Light Emitting Diode), or the like is used. When the quantum efficiency of a sample SMP is to be measured, monochromatic light having a specific single wavelength appropriate for sample SMP to be measured (monochromatic ultraviolet light having a single wavelength in a range of 200 to 400 nm for example) is preferably used as the excitation light. Light source apparatus 60 thus includes a wavelength bandpass filter for selecting target monochromatic light from the light generated by the light source.

The excitation light generated by light source apparatus 60 is directed by an optical fiber 62 to a radiation unit 64 disposed in association with sample window 16. The excitation light is then radiated from radiation unit 64 into the integrating space to propagate along an optical axis Ax1.

On the optical axis of the excitation light in integrator 40, a holding unit 22 is positioned for disposing sample SMP or reference object REF. Holding unit 22 is a tubular casing having a hollow formed at its center, and a translucent container (cell) can be disposed at its central portion. The cell is made of a translucent material, and a liquid sample SMP or reference object REF is enclosed in the cell.

The excitation light radiated from radiation unit 64 passes through the cell held by holding unit 22 to proceed toward the vertex of hemispherical portion 1. Radiation of the excitation light causes a phosphor in sample SMP to be excited, so that fluorescence is generated from the phosphor. The intensity of the generated fluorescence is measured by a method as described later herein.

Reference object REF is typically constituted of a solvent used for preparing liquid-state sample SMP. Namely, the cell in which reference object REF is enclosed corresponds to a cell to which the solvent is added instead of the phosphor in the enclosed liquid-state sample SMP.

Integrator 40 is provided with an observation window 18 formed at a position apart from the center of plane mirror 10. Observation window 18 is provided at a position that does not cross optical axis Ax1 of the excitation light in integrator 40. Quantum efficiency measurement apparatus 400 further includes a measurement device 70 for measuring the illuminance (spectrum) in the integrating space through observation window 18 provided to integrator 40. The illuminance measured through observation window 18 corresponds to the illuminance detected at the inner wall surface of a full-sphere type integrator made up of a space (real image) defined by the inner surface of hemispherical portion 1 and a virtual image created by plane mirror 10.

Figure 2:
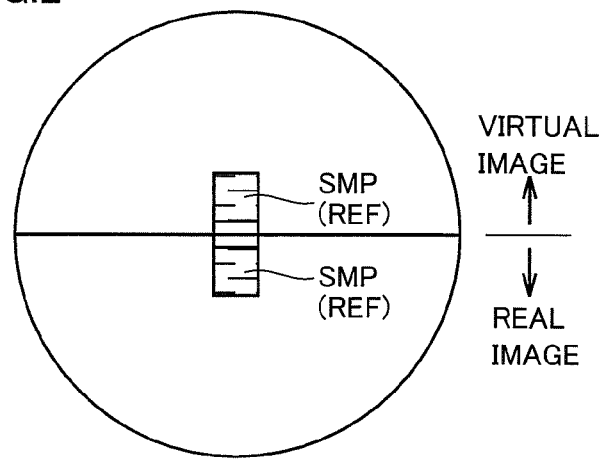
FIG. 2 shows a virtual integrating space created in the quantum efficiency measurement apparatus shown in FIG. 1.

For example, when sample SMP or reference object REF is disposed in integrator 40, a real image and a virtual image of sample SMP or reference object REF are created as shown in FIG. 2. By way of example, when sample SMP having received excitation light emits light, an illuminance distribution is obtained in the integrating space shown in FIG. 2 that is similar to the illuminance distribution obtained when two samples SMPs each emit light.

Referring again to FIG. 1, on the outside of plane mirror 10, a light extraction unit 26 for directing a part of the light in the integrating space through observation window 18 to measurement device 70 is provided. Light extraction unit 26 includes a casing 26a covering observation window 18. In casing 26a, a fiber end 26b connected to optical fiber 26d, for directing light to measurement device 70, are provided. In casing 26a, a reflective portion 26c is provided for converting the direction of propagation of the light entering through observation window 18 by approximately 90° and then directing the light to fiber end 26b.

Measurement device 70 measures the spectrum of the light introduced by optical fiber 26d. Typically, measurement device 70 is configured to include a diffraction grating and a line sensor or the like associated with the directions of diffraction of the diffraction grating to detect the intensity of the input light for each wavelength. When the quantum efficiency of a phosphor is to be measured, the wavelength range of the excitation light applied to sample SMP and the wavelength range of fluorescence generated from sample SMP differ from each other. Therefore, the range of measurement of measurement device 70 is adapted to cover both of the wavelength range of the excitation light applied from light source apparatus 60 and the wavelength range of the fluorescence generated from sample SMP having received excitation light.

Quantum efficiency measurement apparatus 400 includes a processing unit 80 connected to measurement device 70 for calculating the quantum efficiency of sample SMP from the result of detection by measurement device 70. Processing unit 80 is typically a computer having a general architecture, and executes a program (instruction code) installed in advance to provide the function of calculating the quantum efficiency as described later herein. A program providing such a function is stored in a non-transitory storage medium such as CD-ROM (Compact Disc Read Only Memory) and distributed, or delivered via a network. Such a program for calculating the quantum efficiency may be incorporated to be a part of another program and provided. In this case, processing can also be implemented by means of a module provided by the aforementioned other program, and thus the program itself for calculating the quantum efficiency may not include the module provided by the other program.

Further, a part or the whole of functions provided by the program may be implemented by means of a dedicated hardware circuit. For example, all functions provided by processing unit 80 may be incorporated in measurement device 70.

Integrator 40 has an observation window 14 formed at a position located apart from the center of plane mirror 10. Observation window 14 chiefly serves as a window for observing the state in integrator 40 prior to measurement for example, and is closed with a plug member 28 so that no ambient light enters the integrating space at the time of normal measurement.

In quantum efficiency measurement apparatus 400, preferably the whole of integrator 40 is housed in a dark box 8. This is for the reason that, in terms of improvement of the measurement accuracy, it is preferable to limit entrance of ambient light into the integrating space of integrator 40.

b2. Principle of Measurement

Next, a description will be given of a principle and a procedure for measuring the quantum efficiency (internal quantum yield) $\eta_{internal}$ of sample SMP by means of quantum efficiency measurement apparatus 400 shown in FIG. 1.

For measurement of the quantum efficiency by means of quantum efficiency measurement apparatus 400 shown in FIG. 1, on the basis of a spectrum (excitation light spectrum) measured when the excitation light from light source apparatus 60 is applied to reference object REF (solvent only), a spectrum (sample spectrum) measured when the excitation light from light source apparatus 60 is applied to sample SMP (sample+solvent) is evaluated.

Figure 3A:
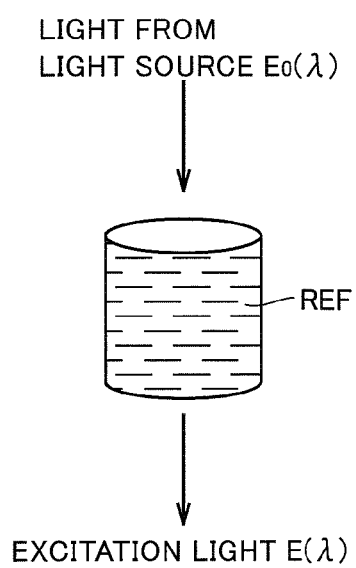
FIGS. 3A and 3B are diagrams for illustrating a principle of measurement of the quantum efficiency.
Figure 3B:
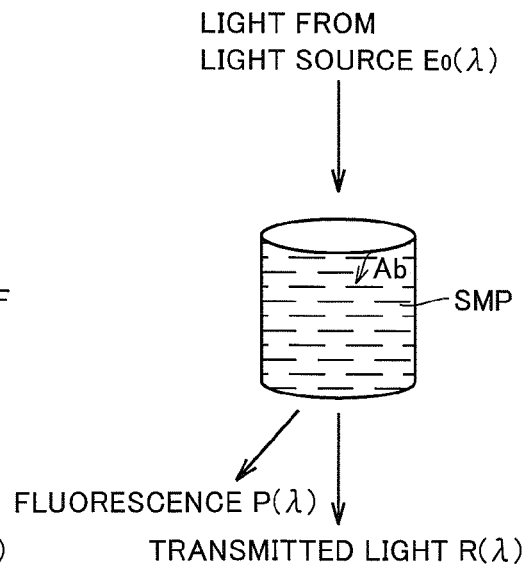

FIG. 3A shows the state where a reference (solvent) is measured, and FIG. 3B shows the state where a sample (solution) is measured. For the quantum efficiency measurement according to the present embodiment, as shown in FIG. 3A, the spectrum measured when the excitation light (light source spectrum $E_0(\lambda)$) from light source apparatus 60 is applied to reference object REF (solvent only) is obtained as excitation light spectrum $E(\lambda)$. This excitation light spectrum $E(\lambda)$ is used as a reference value for calculating the optical energy (excitation energy) absorbed by sample SMP at the time of sample measurement shown in FIG. 3B. Namely, excitation light spectrum $E(\lambda)$ corresponds to optical energy excluding the energy absorbed by the solvent and the container (cell) from the optical energy applied from light source apparatus 60.

Further, as shown in FIG. 3B, the spectrum of the transmitted light measured when the excitation light (light source spectrum $E_0(\lambda)$) from light source apparatus 60 is applied to sample SMP is obtained as transmitted light spectrum $R(\lambda)$. At this time, a phosphor in sample SMP is excited by the excitation light to generate fluorescence (fluorescence spectrum $P(\lambda)$). Thus, the difference between excitation light spectrum $E(\lambda)$ measured when the excitation light has passed through reference object REF (solvent only), and transmitted light spectrum $R(\lambda)$ measured when the excitation light has passed through sample SMP corresponds to the optical energy (absorption energy Ab) consumed for generating fluorescence.

Since the optical energy of fluorescence can be measured from fluorescence spectrum $P(\lambda)$ of the generated fluorescence, the ratio between the optical energy of the fluorescence and the optical energy consumed for generating the fluorescence is the quantum efficiency (internal quantum yield) $\eta_{internal}$. Further, the ratio of transmitted light spectrum $R(\lambda)$ to excitation light spectrum $E(\lambda)$ is the transmittance of the excitation light through sample SMP.

It is assumed for example that the wavelength range of the excitation light generated from light source apparatus 60 is $\lambda_1$ to $\lambda_2$ and the wavelength range of the fluorescence generated from sample SMP is $\lambda_3$ to $\lambda_4$. Then, the quantum efficiency (internal quantum yield) $\eta_{internal}$ may be represented by expression (1) as follows.

$$\eta_{internal} = \frac{\int_{\lambda_3}^{\lambda_4} \lambda \cdot P(\lambda) d\lambda}{\int_{\lambda_1}^{\lambda_2} \lambda \cdot \{E(\lambda) - R(\lambda)\} d\lambda} \quad (1)$$

It is noted that the spectrum is multiplied by $\lambda$ in the denominator and the numerator of expression (1), for the purpose of converting the spectrum (optical intensity) into the number of photons.

Figure 4A:
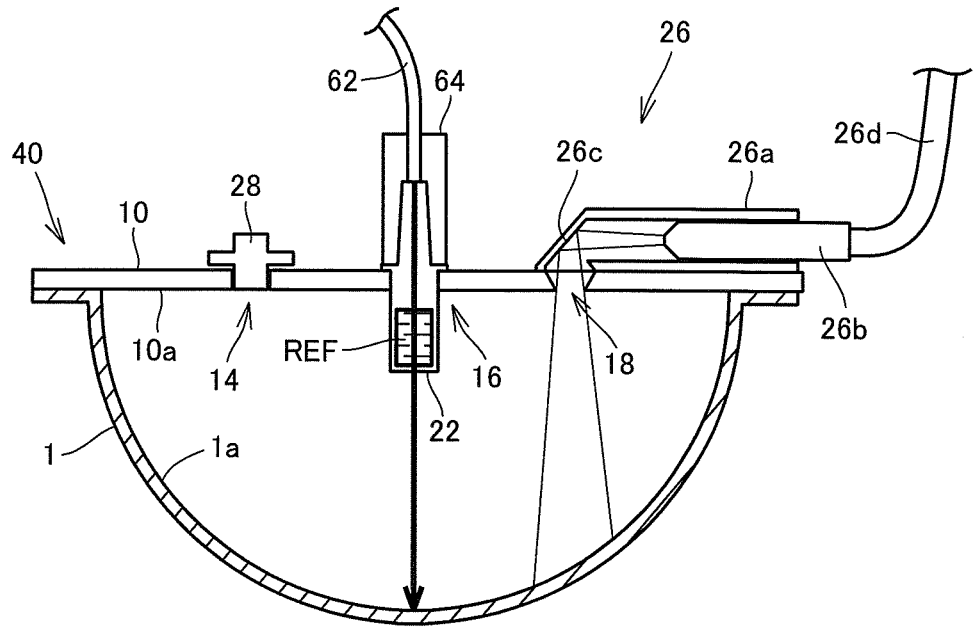
FIGS. 4A and 4B are diagrams for illustrating a procedure for measuring the quantum efficiency of a sample by means of the quantum efficiency measurement apparatus relevant to the present invention.
Figure 4B:
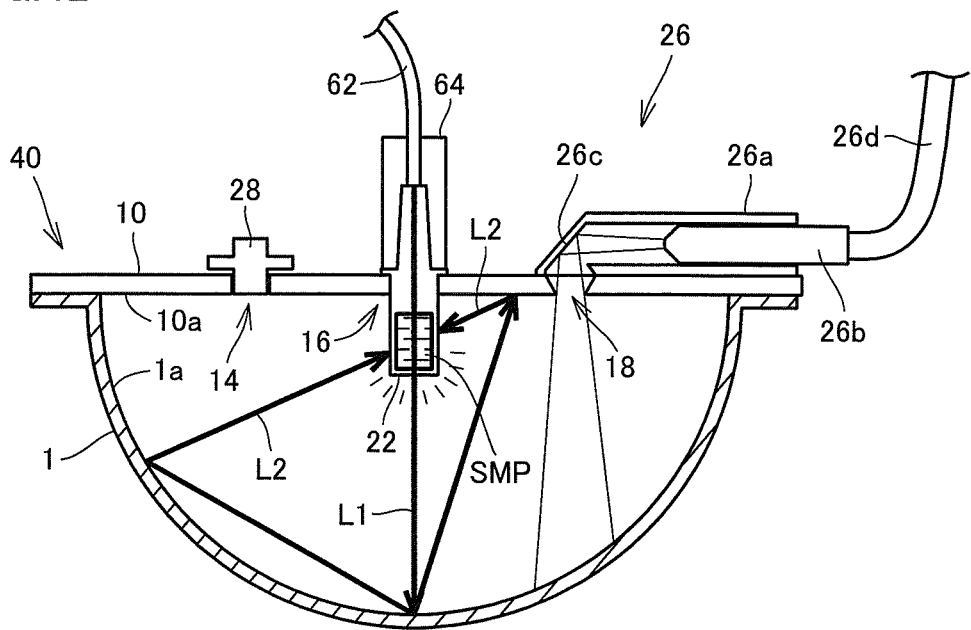

Referring to FIGS. 4A and 4B, a description will be given of a procedure for measuring the quantum efficiency of sample SMP by means of quantum efficiency measurement apparatus 400. FIG. 4A shows the state where a reference (solvent) is measured, and FIG. 4B shows the state where a sample (solution) is measured.

As shown in FIG. 4A, with reference object REF disposed at holding unit 22, excitation light is applied from light source apparatus 60 (FIG. 1) to measure the spectrum (excitation light spectrum $E(\lambda)$) in the integrating space.

Further, as shown in FIG. 4B, with sample SMP disposed at holding unit 22, excitation light is applied from light source apparatus 60 (FIG. 1) to measure the spectrums (transmitted light spectrum $R(\lambda)$ and fluorescence spectrum $P(\lambda)$) in the integrating space. Since quantum efficiency measurement apparatus 400 uses measurement device 70 having a detection range that covers both the wavelength range of the excitation light and that of the fluorescence, transmitted light spectrum $R(\lambda)$ and fluorescence spectrum $P(\lambda)$ can be measured simultaneously under the condition shown in FIG. 4B. When the quantum efficiency of a phosphor is to be measured, ultraviolet light is used as the excitation light and, because the generated fluorescence is visible light, they can easily be separated in the wavelength field.

Figure 5:
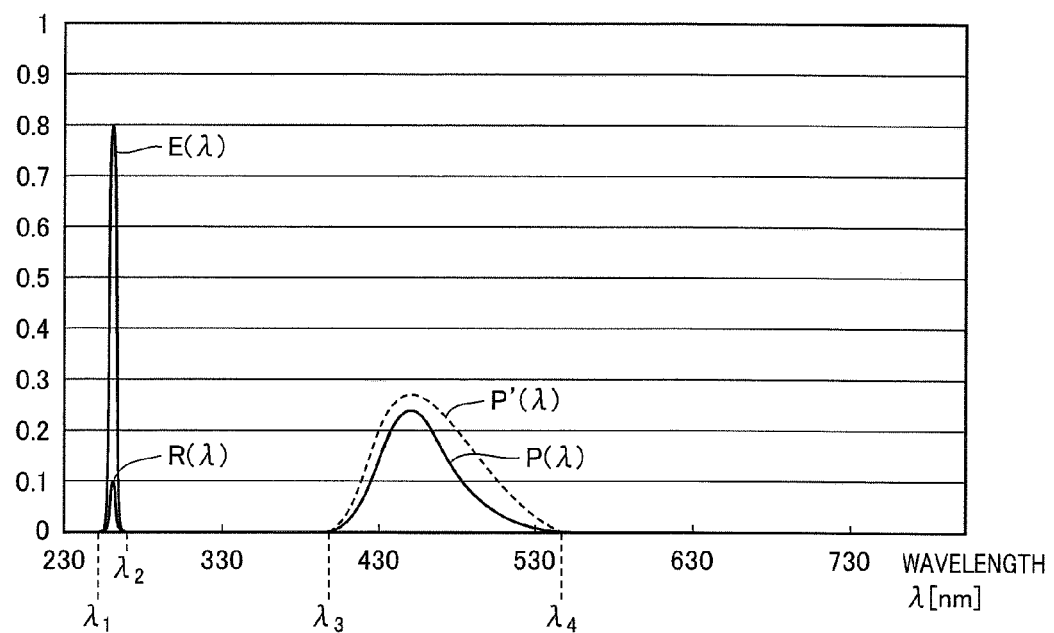
FIG. 5 shows examples of spectrums measured by the measurement procedure shown in FIGS. 4A and 4B.

In other words, measurement shown in FIG. 4A and measurement shown in FIG. 4B are each performed to desirably measure the spectrums as shown in FIG. 5. The measurement shown in FIG. 4A and the measurement shown in FIG. 4B may be performed in any order.

b3. Re-Excitation

Next, re-excitation that accompanies the method of measuring the quantum efficiency as described above will be explained.

Referring again to FIG. 4B, when the excitation light is applied to sample SMP, fluorescence which is generated from the excitation light applied from light source apparatus 60 to directly enter sample SMP (fluorescence generated from primary excitation light L1), and fluorescence which is generated from the excitation light passing through sample SMP and reflected from the inner wall surface or the like of hemispherical portion 1 to re-enter sample SMP (fluorescence generated from secondary excitation light L2) may both be generated. Such generation of the fluorescence from secondary excitation light L2 is also referred to as "re-excitation phenomenon" or "secondary excitation phenomenon".

Consequently, the illuminance detected in the integrating space in integrator 40 is the illuminance of the sum of these fluorescence components. In other words, as shown in FIG. 5, in order to calculate the quantum efficiency, fluorescence spectrum $P(\lambda)$ of the fluorescence generated from primary excitation light L1 should be measured; actually, however, the measured fluorescence spectrum $P'(\lambda)$ is larger by the fluorescence generated from secondary excitation light L2. As a result, the calculated quantum efficiency has a value larger than the value that should intrinsically be calculated.

A quantum efficiency measurement apparatus according to an embodiment of the present invention as illustrated below has an object of reducing measurement errors due to such re-excitation (secondary excitation).

[C. First Embodiment]

c1. Apparatus Configuration

Referring to FIG. 6, the entire configuration of a quantum efficiency measurement apparatus 100 according to a first embodiment of the present invention will be described. Quantum efficiency measurement apparatus 100 shown in FIG. 6 uses a hemispherical integrator 50A to form an integrating space used for measuring the quantum efficiency of sample SMP.

Integrator 50A has an excitation light passage window 12 formed at a vertex portion of hemispherical portion 1. Excitation light passage window 12 is opposite to sample window 16, and located at a portion which crosses optical axis Ax1 of the excitation light in integrator 50A and on which the excitation light is incident. Namely, when excitation light passage window 12 is opened, the component (secondary excitation light) having been applied from light source apparatus 60 and passed through sample SMP will be discharged to the outside of integrator 50A.

In excitation light passage window 12, a plug member 30 having a reflection characteristic which is substantially identical to that of light diffuse reflection layer 1a located on the inner surface of hemispherical portion 1 is fit. Where plug member 30 is fit in excitation light passage window 12 so that excitation light passage window 12 is closed, the component (secondary excitation light) of the excitation light that has been applied from light source apparatus 60 and passed through sample SMP will be diffuse-reflected toward the inside of integrator 50A.

Namely, excitation light passage window 12 and plug member 30 function as a switch mechanism for making a switch between the state of reflecting the excitation light (secondary excitation light) in the integrating space, and the state of non-reflecting the excitation light (secondary excitation light) in the integrating space.

Figure 7A:
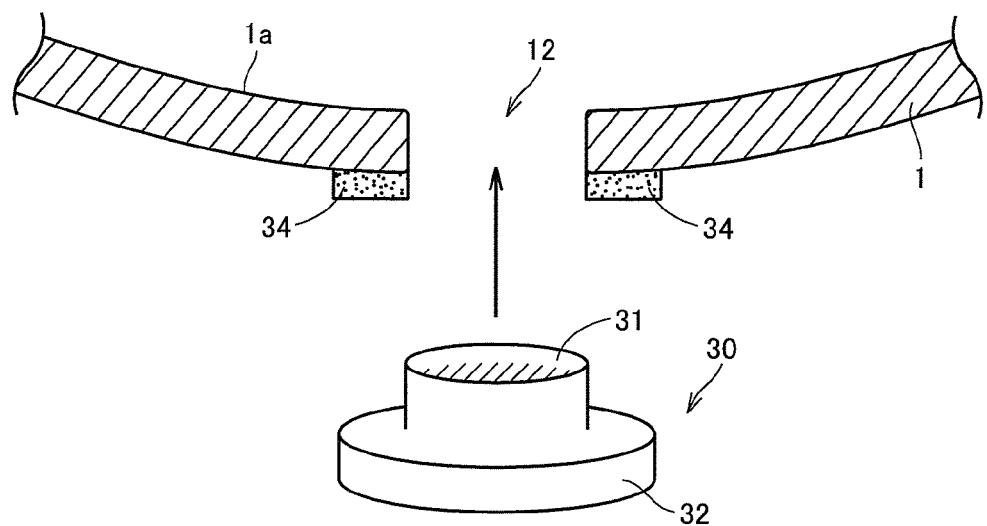
FIGS. 7A and 7B show examples of a more detailed structure of a plug member shown in FIG. 6.
Figure 7B:
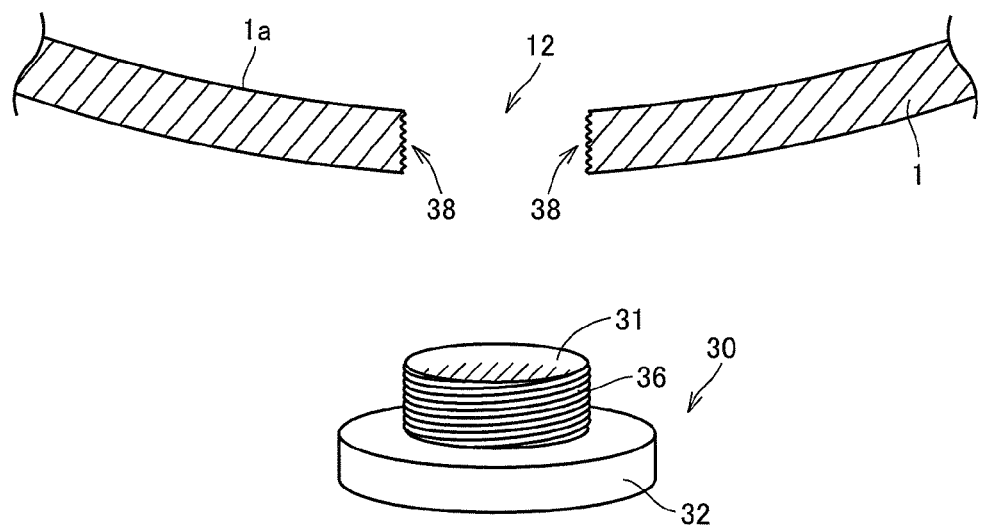

Referring to FIGS. 7A and 7B, examples of a more detailed structure of plug member 30 shown in FIG. 6 will be described. Plug member 30 shown in FIG. 7A is formed of a reflective portion 31 having its radius substantially identical to that of excitation light passage window 12, and a base material 32. On the surface, which faces the integrating space, of reflective portion 31, a reflection layer made of a diffusing material (such as sintered PTFE, barium sulfate or the like) similar to that for light diffuse reflection layer 1a of hemispherical portion 1 is formed. Therefore, as plug member 30 is fit in excitation light passage window 12, the integrating space provided by integrator 50A is substantially identical to the integrating space provided by integrator 40 of quantum efficiency measurement apparatus 400 shown in FIG. 1.

As an example of a means for fitting plug member 30 in excitation light passage window 12, FIG. 7A shows a structure where a magnet 34 provided around the perimeter of excitation light passage window 12 is used. Specifically, base material 32 of plug member 30 is made of a metal, and the magnetic force between base material 32 and magnet 34 joins plug member 30 to hemispherical portion 1.

In an alternative structure, hemispherical portion 1 and plug member 30 may be joined by screwing so as to close excitation light passage window 12. Specifically, as shown in FIG. 7B, a screw groove 36 is formed on the outer periphery of reflective portion 31 of plug member 30, and a screw groove 38 to engage with screw groove 36 is formed on the inner periphery of excitation light passage window 12. In this way, plug member 30 can be fit and secured in excitation light passage window 12.

In terms of enhancement of the integrating efficiency of integrator 50A, it is preferable that the area of the opening of excitation light passage window 12 is made as small as possible. By way of example, the standard of "Electrical and Photometric Measurements of Solid-State Lighting Products" defined as LM-79-08 of IES (Illuminating Engineering Society of North America) recommends that the area of the reflection layer in the integrator should be 90% to 98%. For example, in order to keep the area of the reflection layer in the integrator at 98%, a relational expression like expression (2) must be satisfied where R is the radius of curvature of hemispherical portion 1 and r is the radius of excitation light passage window 12. It is noted that a virtual image of excitation light passage window 12 is also created by hemispherical integrator 40, and therefore the area of the opening of excitation light passage window 12 is doubled in expression (2).

$$2 \times \pi r^2 / 4\pi R^2 \leq 0.02 \qquad (2)$$

$$r/R \leq 0.2$$

Namely, radius r of excitation light passage window 12 is preferably set to 20% or less of the radius of curvature R of hemispherical portion 1.

It is supposed for example that the excitation light emitted from radiation unit 64 has a square cross section of 7 mm×7 mm. Here, when the radius of curvature of hemispherical portion 1 is approximately 7 cm (diameter φ: 5.5 inches), radius r of excitation light passage window 12 is 14 mm (diameter φ: 16.8 mm). Namely, the maximum allowable size of excitation light passage window 12 is sufficiently larger than the excitation light having the cross section of 7 mm×7 mm. Further, when the radius of curvature of hemispherical portion 1 is approximately 4.2 cm (diameter φ: 3.3 inches), radius r of excitation light passage window 12 is 8.4 mm (diameter φ: 16.8 mm). In this case as well, the maximum allowable size of excitation light passage window 12 is sufficiently larger than the cross-sectional area of the excitation light.

As seen from the above, even when excitation light passage window 12 as described above is provided, the resultant influence on the accuracy of measurement is practically negligible.

It is noted that radiation unit 64 may be provided with an optical system for converting the excitation light into parallel light. Such an optical system can be employed to prevent the beam diameter of the excitation light transmitted through sample SMP and reference object REF from increasing.

Quantum efficiency measurement apparatus 100 according to the first embodiment of the present invention shown in FIG. 6 is similar to quantum efficiency measurement apparatus 400 relevant to the present invention shown in FIG. 1 except that excitation light passage window 12 is formed at a vertex portion of hemispherical portion 1, and therefore, the detailed description of other elements will not be repeated.

c2. Principle of Measurement

Next, a principle and a procedure for measuring the quantum efficiency (internal quantum yield) $\eta_{internal}$ by means of quantum efficiency measurement apparatus 100 shown in FIG. 6 will be described.

For measurement of the quantum efficiency by means of quantum efficiency measurement apparatus 100 shown in FIG. 6, first to third spectrums measured respectively in the following three states are used.

(1) First spectrum $E^{(1)}(\lambda)$: Sample SMP is disposed at holding unit 22, and excitation light passage window 12 is set in a state of reflecting secondary excitation light (state where plug member 30 is fit in the window).

(2) Second spectrum $E^{(2)}(\lambda)$: Sample SMP is disposed at holding unit 22 and excitation light passage window 12 is set in a state of non-reflecting secondary excitation light (state where plug member 30 is detached).

(3) Third spectrum $E^{(3)}(\lambda)$: Reference object REF is disposed at holding unit 22 and excitation light passage window 12 is set in a state of reflecting secondary excitation light (state where plug member 30 is fit in the window).

First to third spectrums $E^{(1)}(\lambda)$ to $E^{(3)}(\lambda)$ measured in the above-described manner are used to calculate transmitted light spectrum R ($\lambda$), fluorescence spectrum P ($\lambda$), and excitation light spectrum E ($\lambda$), respectively.

Figure 8:
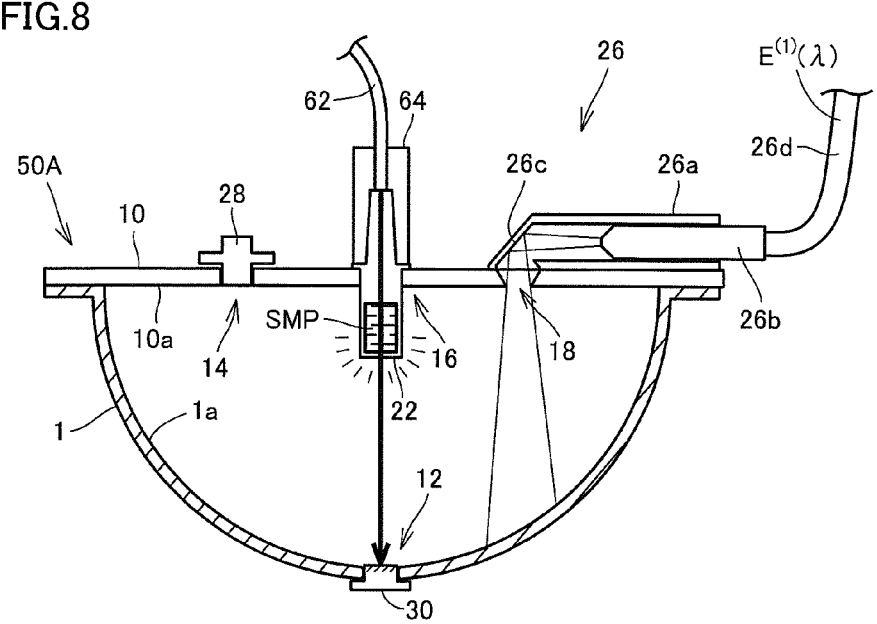
FIG. 8 shows a state where a first spectrum is measured by means of the quantum efficiency measurement apparatus according to the first embodiment of the present invention.
Figure 9:
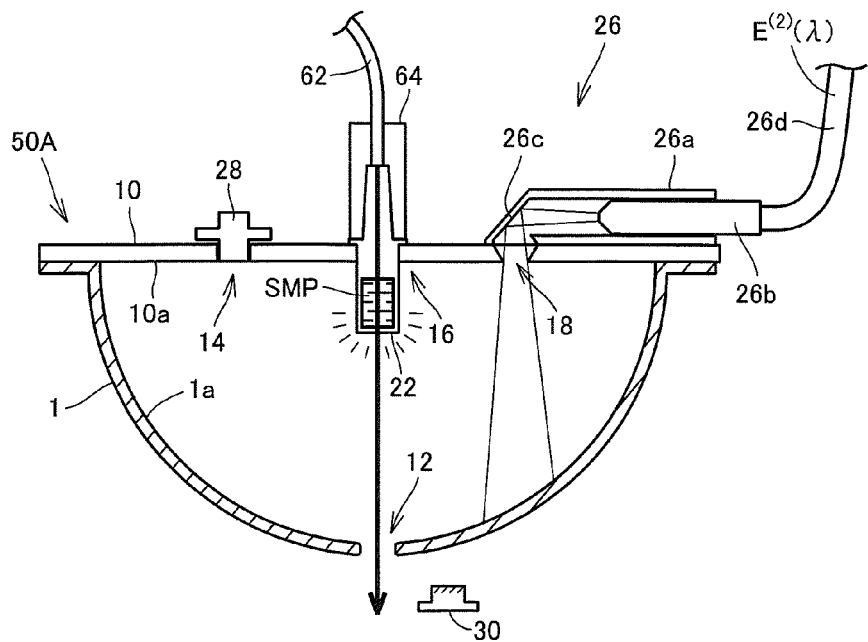
FIG. 9 shows a state where a second spectrum is measured by means of the quantum efficiency measurement apparatus according to the first embodiment of the present invention.
Figure 10:
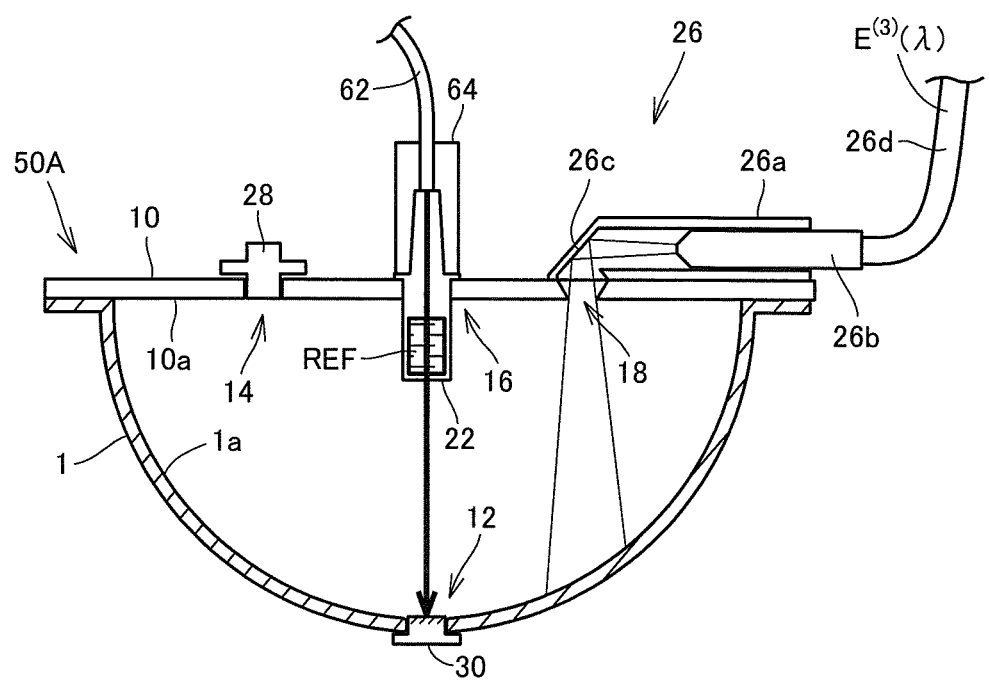
FIG. 10 shows a state where a third spectrum is measured by means of the quantum efficiency measurement apparatus according to the first embodiment of the present invention.

FIG. 8 shows a state of measuring first spectrum $E^{(1)}(\lambda)$ by means of quantum efficiency measurement apparatus 100. FIG. 9 shows a state of measuring second spectrum $E^{(2)}(\lambda)$ by means of quantum efficiency measurement apparatus 100. FIG. 10 shows a state of measuring third spectrum $E^{(3)}(\lambda)$ by means of quantum efficiency measurement apparatus 100.

As shown in FIG. 8, first spectrum $E^{(1)}(\lambda)$ is measured in the state where sample SMP is disposed at holding unit 22 and plug member 30 is fit in excitation light passage window 12 so that secondary excitation light is reflected. Of the measured first spectrum $E^{(1)}(\lambda)$, the component in the wavelength range ($\lambda_1$ to $\lambda_2$) of the excitation light is calculated as transmitted light spectrum R ($\lambda$) shown in FIG. 5.

As shown in FIG. 9, second spectrum $E^{(2)}(\lambda)$ is measured in the state where sample SMP is disposed at holding unit 22 and plug member 30 is detached from excitation light passage window 12 so that secondary excitation light is not reflected. Of the measured second spectrum $E^{(2)}(\lambda)$, the component in the wavelength range ($\lambda_3$ to $\lambda_4$) of the fluorescence is calculated as fluorescence spectrum P ($\lambda$) shown in FIG. 5.

As shown in FIG. 10, third spectrum $E^{(3)}(\lambda)$ is measured in the state where reference object REF is disposed at holding unit 22 and plug member 30 is fit in excitation light passage window 12 so that secondary excitation light is reflected. Of the measured third spectrum $E^{(3)}(\lambda)$, the component in the wavelength range ($\lambda_1$ to $\lambda_2$) of the excitation light is calculated as excitation light spectrum E ($\lambda$) shown in FIG. 5.

Then, processing unit 80 uses transmitted light spectrum R ($\lambda$), fluorescence spectrum P ($\lambda$), and excitation light spectrum E ($\lambda$) that have been calculated through the above-described procedures to calculate the quantum efficiency (internal quantum yield) $\eta_{internal}$ of sample SMP.

In other words, in the first embodiment of the present invention, transmitted light spectrum R ($\lambda$) is measured as shown in FIG. 8 by the method similar to above-described quantum efficiency measurement apparatus 400 relevant to the present invention (see FIG. 4B), while fluorescence spectrum P ($\lambda$) is measured in the state where re-excitation (secondary excitation) of sample SMP does not occur as shown in FIG. 9. The measurements can thus be taken in two stages to reduce errors due to re-excitation (secondary excitation).

It is noted that for the spectrum to be measured in the state where excitation light is repeatedly reflected in the integrator as shown in FIGS. 8 and 10, it is preferable to perform energy calibration in advance. For this energy calibration, light having a known spectral energy is applied to the integrator and, based on the spectrum measured at this time, the measured spectrum is corrected. In this way, the optical energy (excitation energy) absorbed by sample SMP can accurately be measured.

c3. Procedure of Measurement

Referring to FIG. 11, a user prepares quantum efficiency measurement apparatus 100 and also prepares a cell in which sample SMP to be measured is enclosed and a cell in which reference object REF is enclosed (step S2). Then, above-described first to third spectrums $E^{(1)}(\lambda)$ to $E^{(3)}(\lambda)$ are measured. It is noted that the order in which the spectrums are measured is not particularly limited, as long as the three spectrums have finally been measured at the time when the quantum efficiency is calculated. FIG. 11 shows an example where the measurements are taken in the order of the first, second, and third spectrums.

In step S10, the user disposes sample SMP at holding unit 22 of integrator 50A. Namely, the user disposes sample SMP at a predetermined position in the integrating space of integrator 50A. At this time, observation window 14 of integrator 50A is closed with plug member 28.

In subsequent step S12, the user measures the spectrum for sample SMP. Specifically, excitation light from light source apparatus 60 is applied to sample SMP through sample window 16 of integrator 50A, and the spectrum in the integrating space is measured by measurement device 70 through observation window 18 of integrator 50A. The spectrum measured by measurement device 70 is first spectrum $E^{(1)}(\lambda)$.

In subsequent step S14, processing unit 80 stores the data of spectrum $E^{(1)}(\lambda)$ measured by measurement device 70.

In step S20, with sample SMP kept disposed at holding unit 22 of integrator 50A, the user configures the excitation light incident portion (excitation light passage window 12) crossed by optical axis Ax1 of the excitation light in integrator 50A, so that excitation light having passed through sample SMP (secondary excitation light) is not reflected in the integrating space. Namely, the user changes the state where excitation light passage window 12 for allowing the secondary excitation light to pass therethrough is closed with plug member 30 to the state where plug member 30 is detached.

In subsequent step S22, the user measures the spectrum for sample SMP. Specifically, the excitation light from light source apparatus 60 is applied to sample SMP through sample window 16 of integrator 50A, and the spectrum in the integrating space is measured by measurement device 70 through observation window 18 of integrator 50A. This spectrum measured by measurement device 70 is second spectrum $E^{(2)}(\lambda)$.

In subsequent step S24, processing unit 80 stores the data of second spectrum $E^{(2)}(\lambda)$ measured by measurement device 70.

In step S30, the user disposes reference object REF at holding unit 22 of integrator 50A. Namely, the user disposes reference object REF at a predetermined position in the integrating space of integrator 50A.

In subsequent step S32, the user configures the excitation light incident portion (excitation light passage window 12) crossed by optical axis Ax1 of the excitation light in integrator 50A, so that the excitation light after having passed through reference object REF is reflected in the integrating space. Namely, the user changes the state where excitation light passage window 12 for allowing the secondary excitation light to pass therethrough is opened to the state where the window is closed with plug member 30.

In subsequent step S34, the user measures the spectrum for reference object REF. Specifically, the excitation light from light source apparatus 60 is applied to reference object REF through sample window 16 of integrator 50A, and the spectrum in the integrating space is measured by measurement device 70 through observation window 18 of integrator 50A. This spectrum measured by measurement device 70 is third spectrum $E^{(3)}(\lambda)$.

In subsequent step S36, processing unit 80 stores the data of third spectrum $E^{(3)}(\lambda)$ measured by measurement device 70.

Through the above-described process, first to third spectrums $E^{(1)}(\lambda)$ to $E^{(3)}(\lambda)$ are measured, and then the process of calculating the quantum efficiency by processing unit 80 is executed.

In step S40, processing unit 80 calculates the component which is a constituent part of first spectrum $E^{(1)}(\lambda)$ and corresponds to the wavelength range of the excitation light, as transmitted light spectrum R ($\lambda$). In subsequent step S42, processing unit 80 calculates the component which is a constituent part of second spectrum $E^{(2)}(\lambda)$ and corresponds to the wavelength range of the fluorescence, as fluorescence spectrum P ($\lambda$). In subsequent step S44, processing unit 80 calculates the component which is a constituent part of third spectrum $E^{(3)}(\lambda)$ and corresponds to the wavelength range of the excitation light, as excitation light spectrum E ($\lambda$).

In step S46, processing unit 80 uses transmitted light spectrum R ($\lambda$), fluorescence spectrum P ($\lambda$), and excitation light spectrum E ($\lambda$) that are calculated in steps S40 to S44 to calculate the quantum efficiency (internal quantum yield) $\eta_{internal}$ of sample SMP following above-described expression (1). At this time, processing unit 80 calculates the difference between transmitted light spectrum R ($\lambda$) which is a constituent part of first spectrum $E^{(1)}(\lambda)$ and corresponds to the excitation light, and excitation light spectrum E ($\lambda$) which is a constituent part of third spectrum $E^{(3)}(\lambda)$ and corresponds to the excitation light, as the optical component absorbed by sample SMP.

In step S48, processing unit 80 outputs the value of calculated quantum efficiency (internal quantum yield) $\eta_{internal}$. It is noted that the value may be output in such a manner that displays the value on a display or the like connected to processing unit 80, a manner that transmits the value to a host computer or the like connected to processing unit 80, a manner that prints out the value by means of a printer or the like connected to processing unit 80, or the like.

As described above, first to third spectrums $E^{(1)}(\lambda)$ to $E^{(3)}(\lambda)$ may be measured in any order. Specifically, the order may be changed between a group of steps S10 to S14, a group of steps S20 to S24, and a group of steps S30 to S36 shown in FIG. 11. Further, in the case where multiple samples SMPs are successively measured, the process of calculating excitation light spectrum E ($\lambda$) from steps S30 to S36 may be performed only once and, for multiple samples SMPs, the calculated excitation light spectrum E ($\lambda$) may commonly be used.

c4. Modification

The first embodiment has been described herein in connection with the case where plug member 30 is detached when second spectrum $E^{(2)}(\lambda)$ is to be measured. Alternatively, a member that absorbs the excitation light so that the ambient light does not enter the integrating space may be attached.

Figure 12A:
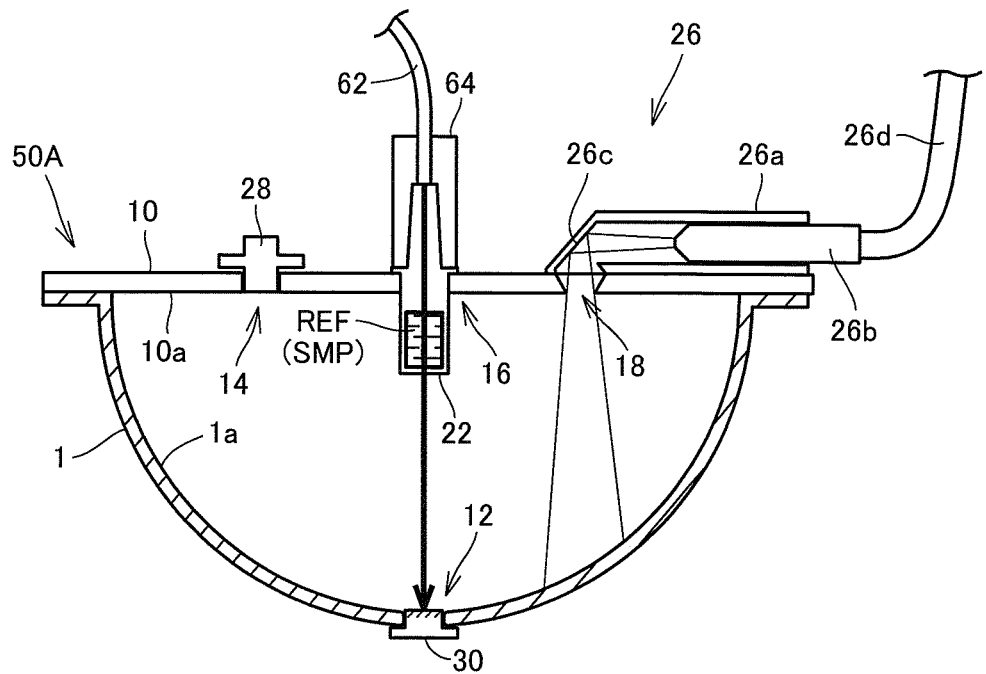
FIGS. 12A and 12B are diagrams for illustrating a procedure for measuring the quantum efficiency of a sample by means of a quantum efficiency measurement apparatus according to a modification of the first embodiment of the present invention.
Figure 12B:
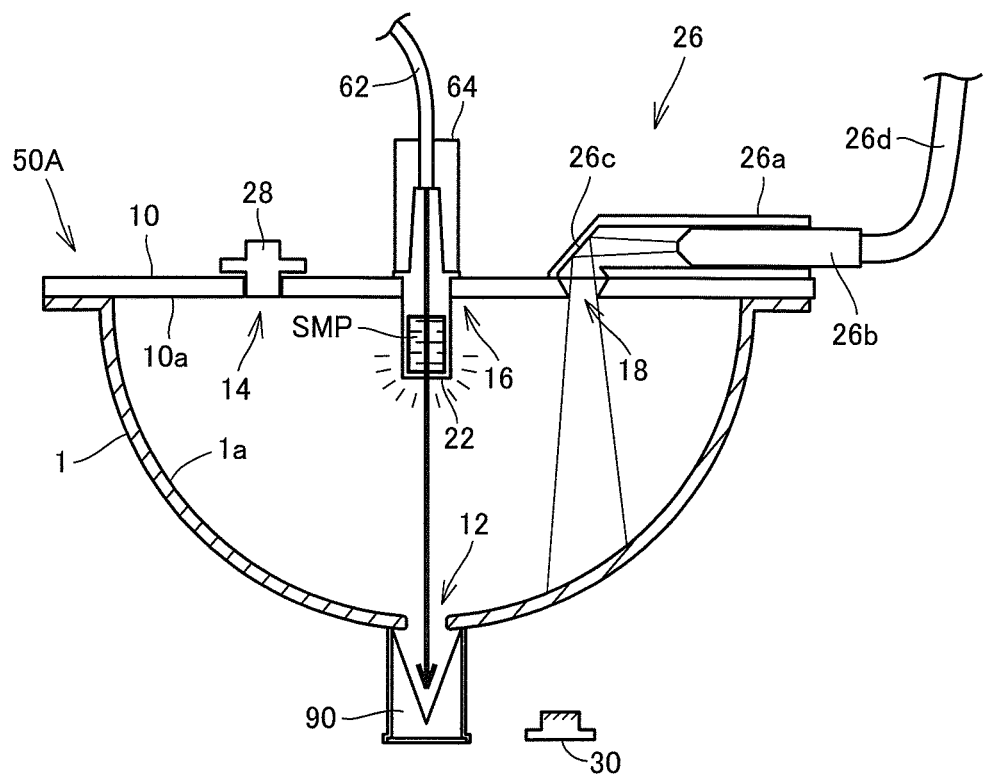

Referring to FIGS. 12A and 12B, a description will be given of a procedure for measuring the quantum efficiency of sample SMP by means of a quantum efficiency measurement apparatus according to a modification of the first embodiment of the present invention. In particular, FIG. 12A shows a state of measuring first spectrum $E^{(1)}(\lambda)$ and third spectrum $E^{(3)}(\lambda)$, and FIG. 12B shows a state of measuring second spectrum $E^{(2)}(\lambda)$.

Specifically, the state of measuring first spectrum $E^{(1)}(\lambda)$ and third spectrum $E^{(3)}(\lambda)$ shown in FIG. 12A is similar to that shown in FIGS. 8 and 10 as described above. In contrast, in the state of measuring second spectrum $E^{(2)}(\lambda)$ shown in FIG. 12B, a light absorbing portion 90 is attached from the outside of an integrator 50A, in association with excitation light passage window 12.

Light absorbing portion 90 is typically an optical device called light trap, and absorbs secondary excitation light having passed through excitation light passage window 12 so that the secondary excitation light is not reflected in the integrating space. At the same time, light absorbing portion 90 also performs the function of preventing ambient light from entering the integrating space through excitation light passage window 12.

Alternatively, an optical device that selectively absorbs light in the wavelength range of the excitation light may be attached to excitation light passage window 12. In this case, only the secondary excitation light is absorbed, while the fluorescence generated from sample SMP is reflected at excitation light passage window 12.

[D. Second Embodiment]

Figure 13:
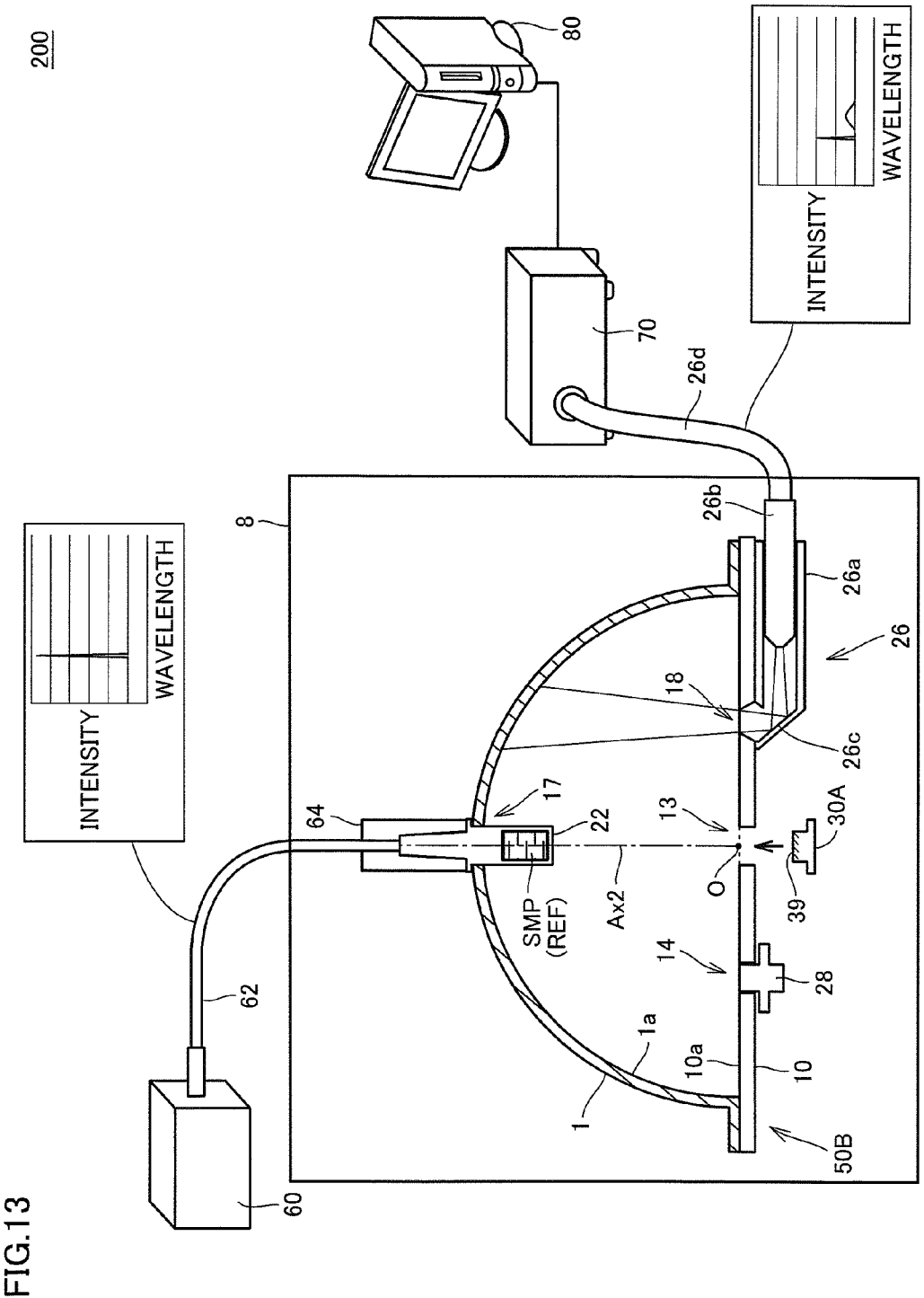
FIG. 13 is a schematic diagram showing an entire configuration of a quantum efficiency measurement apparatus according to a second embodiment of the present invention.

Referring to FIG. 13, an entire configuration of a quantum efficiency measurement apparatus 200 according to a second embodiment of the present invention will be described. Quantum efficiency measurement apparatus 200 shown in FIG. 13 corresponds to quantum efficiency measurement apparatus 100 shown in FIG. 6 in which the positional relationship between excitation light passage window 12 and sample window 16 in integrator 50A is changed so that respective positions are replaced with each other.

Specifically, in an integrator 50B, an excitation light passage window 13 for allowing secondary excitation light to pass through is formed at a central portion of plane mirror 10, and a sample window 17 for allowing the excitation light to be applied into the integrating space is formed at a vertex portion of hemispherical portion 1. Excitation light passage window 13 is opposite to sample window 17 and located at a portion which is crossed by an optical axis Ax2 of the excitation light in integrator 50B and on which the excitation light is incident. When excitation light passage window 13 is opened, a component of the excitation light applied from light source apparatus 60 that has passed through sample SMP (secondary excitation light) and propagated along optical axis Ax2 will be discharged to the outside of integrator 50B.

Quantum efficiency measurement apparatus 200 according to the second embodiment of the present invention as shown in FIG. 13 is similar to quantum efficiency measurement apparatus 100 relevant to the present invention as shown in FIG. 6 except for the above-described features, and therefore, the detailed description of other elements will not be repeated. Further, the procedure for measuring the quantum efficiency for example is also similar to that of the above-described first embodiment, and the detailed description will not be repeated.

[E. Third Embodiment]

The above-described first and second embodiments have been illustrated in conjunction with the configuration where the hemispherical integrator is used. Measurements, however, may also be taken similarly by means of a full-sphere type integrator.

Figure 14:
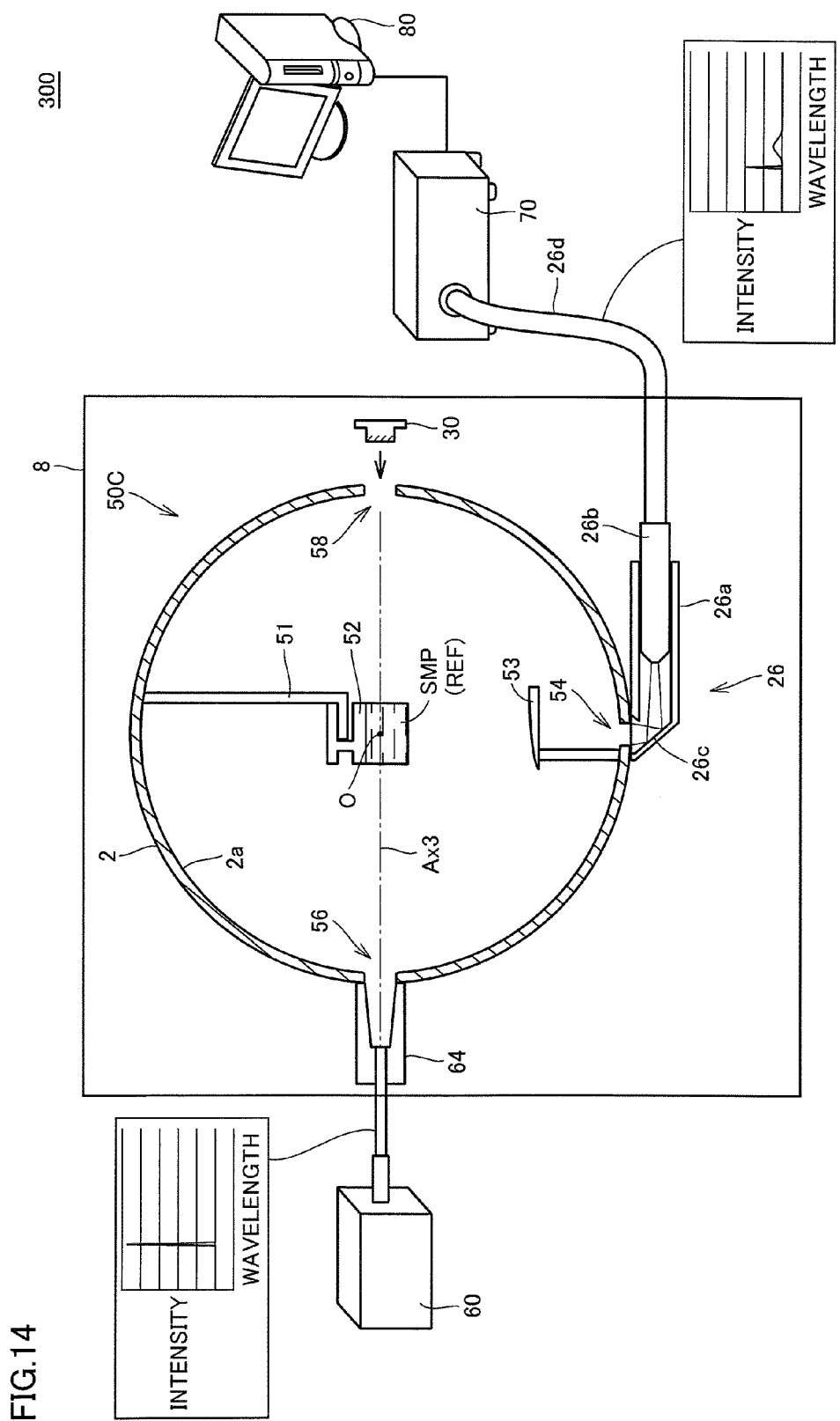
FIG. 14 is a schematic diagram showing an entire configuration of a quantum efficiency measurement apparatus according to a third embodiment of the present invention.

Referring to FIG. 14, an entire configuration of a quantum efficiency measurement apparatus 300 according to a third embodiment of the present invention will be described. Quantum efficiency measurement apparatus 300 shown in FIG. 14 uses a full-sphere type integrator 50C to form an integrating space for measuring the quantum efficiency of sample SMP.

Integrator 50C includes a full-sphere portion 2 having a light diffuse reflection layer 2a on its inner surface (inner wall). This light diffuse reflection layer 2a is formed exemplarily by applying or spraying a light diffusing material such as barium sulfate or PTFE.

Integrator 50C includes, on an optical axis Ax3 passing a substantial center of curvature O of the inner surface of the integrator, a radiation window 56 for radiating excitation light from light source apparatus 60 into the integrating space, and an excitation light passage window 58 for discharging the secondary excitation light having passed through sample SMP to the outside of integrator 50C that are formed opposite to each other. In excitation light passage window 58, a plug member 30 having its reflection characteristic substantially identical to that of light diffuse reflection layer 2a on the inner surface of full-sphere portion 2 is fit. Where plug member 30 is fit in excitation light passage window 58 and accordingly excitation light passage window 58 is closed, a component (secondary excitation light) that is a constituent part of the excitation light applied from light source apparatus 60 and has passed through sample SMP will be diffuse-reflected in integrator 50C.

Namely, excitation light passage window 58 and plug member 30 serve as a switch mechanism for making a switch between the state of reflecting the excitation light (secondary excitation light) in the integrating space, and the state of non-reflecting the excitation light (secondary excitation light) in the integrating space.

In integrator 50C, a holding unit 51 for disposing sample SMP or reference object REF on optical axis Ax3 of the excitation light in the integrator is provided, and a cell 52 in which liquid-state sample SMP or reference object REF is enclosed is hung in the integrating space by means of holding unit 51. Namely, holding unit 51 is configured so that sample SMP and reference object REF can be disposed at a central portion of spherical integrator 50C.

Integrator 50C has an observation window 54 formed at a position that does not cross optical axis Ax3 of the excitation light. Through this observation window 54, the illuminance (spectrum) in the integrating space is measured. Namely, fluorescence generated from excitation light applied to sample SMP is multi-reflected from the inner surface of integrator 50C and thereby integrated (homogenized). A part of this light is directed from light extraction unit 26 to measurement device 70 through observation window 54. It is noted that a baffle 53 is provided between holding unit 51 and observation window 54 so that the fluorescence generated from sample SMP will not directly enter observation window 54.

Similarly to the above-described quantum efficiency measurement by quantum efficiency measurement apparatuses 100 and 200, the quantum efficiency measurement by means of quantum efficiency measurement apparatus 300 also uses first to third spectrums that are measured respectively in the following three states.

(1) First spectrum $E^{(1)}(\lambda)$: Cell 52 in which sample SMP is enclosed is disposed at holding unit 51, and excitation light passage window 58 is set in the state of reflecting secondary excitation light (state where plug member 30 is fit in the window).

(2) Second spectrum $E^{(2)}(\lambda)$: Cell 52 in which sample SMP is enclosed is disposed at holding unit 51, and excitation light passage window 58 is set in the state of non-reflecting secondary excitation light (state where plug member 30 is detached).

(3) Third spectrum $E^{(3)}(\lambda)$: Cell 52 in which reference object REF is enclosed is disposed at holding unit 51, and excitation light passage window 58 is set in the state of reflecting secondary excitation light (state where plug member 30 is fit in the window).

First to third spectrums $E^{(1)}(\lambda)$ to $E^{(3)}(\lambda)$ measured in the above-described manner are used to calculate transmitted light spectrum $R(\lambda)$, fluorescence spectrum $P(\lambda)$, and excitation light spectrum $E(\lambda)$, respectively. These spectrums having been calculated are used to calculate the quantum efficiency of sample SMP.

The specific procedure for measuring the quantum efficiency is similar to that of the above-described first embodiment, and the detailed description thereof will not be repeated.

[F. Conclusion]

In the quantum efficiency measurement method according to the present embodiments, the excitation light (transmitted light spectrum) absorbed by sample SMP is measured in the state where secondary excitation light having been transmitted through sample SMP is reflected in the integrating space, and the fluorescence spectrum generated from sample SMP is measured in the state where the secondary excitation light having been transmitted through sample SMP is not reflected in the integrating space. The fluorescence spectrum thus measured is not influenced by re-excitation (secondary excitation). In this way, as to the quantum efficiency to be measured, errors due to re-excitation (secondary excitation) can be reduced.

Further, in the quantum efficiency measurement apparatus according to the present embodiments, the state where the secondary excitation light having passed through sample SMP is reflected in the integrating space, and the state where the secondary excitation light having passed through sample SMP is not reflected in the integrating space can easily be switched to and from each other merely by attaching (fitting) or detaching the plug member to or from the excitation light passage window provided to the integrator. In this way, the time taken for measurement of the quantum efficiency of sample SMP can be shortened.

Although the present invention has been described and illustrated in detail, it is clearly understood that the same is by way of illustration and example only and is not to be taken by way of limitation, the scope of the present invention being interpreted by the terms of the appended claims.

What is claimed is:

1. A quantum efficiency measurement method comprising the steps of:

disposing a sample at a predetermined position in an integrator having an integrating space;

applying excitation light to said sample disposed at said predetermined position, through a first window provided at said integrator, and measuring a spectrum in said integrating space as a first spectrum, through a second window provided at a position of said integrator, the position of said integrator not being crossed by an optical axis of said excitation light;

configuring an excitation light incident portion located opposite to said first window and crossed by the optical axis of said excitation light in said integrator, so that excitation light after having passed through said sample is not reflected in said integrating space;

applying said excitation light to said sample disposed at said predetermined position through said first window and measuring a spectrum in said integrating space as a second spectrum through said second window, under a state where the excitation light is not reflected in said integrating space; and calculating a quantum efficiency of said sample based on a component constituting a part of said first spectrum and corresponding to a wavelength range of said excitation light, and a component constituting a part of said second spectrum and corresponding to a wavelength range of light generated by said sample from said excitation light received by said sample.

2. The quantum efficiency measurement method according to claim 1, wherein said excitation light incident portion of said integrator has a third window formed to pass said excitation light, and said step of configuring includes the step of removing a plug member having closed said third window, said plug member having a reflection characteristic substantially identical to that of an inner surface of said integrator.

3. The quantum efficiency measurement method according to claim 1, further comprising the steps of:

disposing a reference object at said predetermined position; and applying said excitation light to said reference object disposed at said predetermined position through said first window, and measuring a spectrum in said integrating space as a third spectrum through said second window, wherein said step of calculating a quantum efficiency of said sample includes the step of calculating, as an optical component absorbed by said sample, a difference between a component constituting a part of said first spectrum and corresponding to the wavelength range of said excitation light, and a component constituting a part of said third spectrum and corresponding to the wavelength range of said excitation light.

4. A quantum efficiency measurement apparatus comprising:

an integrator having an integrating space in said integrator;

a light source for applying excitation light into said integrating space through a first window provided at said integrator;

a measurement device for measuring a spectrum in said integrating space through a second window provided at a position of said integrator, the position of said integrator not being crossed by an optical axis of said excitation light;

a holding unit for disposing a sample or a reference object on the optical axis of said excitation light in said integrator;

a switch mechanism for switching an excitation light incident portion located opposite to said first window and being crossed by the optical axis of said excitation light in said integrator, between a state of reflecting said excitation light in said integrating space and a state of non-reflecting said excitation light in said integrating space; and a processing unit for calculating a quantum efficiency of said sample, based on a first spectrum measured by said measurement device when said sample is disposed at said holding unit and said excitation light incident portion is set in the state of reflecting said excitation light, and a second spectrum measured by said measurement device when said sample is disposed at said holding unit and said excitation light incident portion is set in the state of non-reflecting said excitation light.

5. The quantum efficiency measurement apparatus according to claim 4, wherein said switch mechanism includes a third window provided at said excitation light incident portion of said integrator for passing said excitation light, and a plug member to be fit in said third window and having a reflection characteristic substantially identical to an inner surface of said integrator.

6. The quantum efficiency measurement apparatus according to claim 5, wherein said switch mechanism further includes a light absorbing portion attached from outside said integrator and in association with said third window.

7. The quantum efficiency measurement apparatus according to claim 4, wherein said integrator includes:

a hemispherical portion having a light diffuse reflection layer on an inner surface of the hemispherical portion; and a plane mirror disposed to close an opening of said hemispherical portion, and said first window is provided at one of a position involving a substantial center of curvature of said hemispherical portion and located on said plane mirror, and a position involving a vertex of said hemispherical portion.

8. The quantum efficiency measurement apparatus according to claim 4, wherein said integrator is a sphere having a light diffuse reflection layer on an inner surface of the sphere, and said holding unit is configured to allow said sample and said reference object to be disposed at a central portion of said sphere.

9. An integrator having an integrating space in the integrator, comprising:

a holding unit for disposing a sample or a reference object on an optical axis of excitation light applied into said integrating space through a first window;

a light extraction unit for directing light through a second window provided at a position not being crossed by the optical axis of said excitation light so as to measure a spectrum in said integrating space; and a switch mechanism for switching an excitation light incident portion located opposite to said first window and being crossed by the optical axis of said excitation light in said integrator, between a state of reflecting said excitation light in said integrating space and a state of non-reflecting said excitation light in said integrating space.

* * * * *